United States Patent
Raimondi

[19]

[11] Patent Number: 5,941,583
[45] Date of Patent: Aug. 24, 1999

[54] CONTACT LENS INSERTION AND MANIPULATION ASSEMBLY AND METHOD

[76] Inventor: Kent Raimondi, 1322 Greenlakr Dr., Cardiff, Calif. 92007

[21] Appl. No.: 09/166,380

[22] Filed: Oct. 5, 1998

Related U.S. Application Data

[60] Provisional application No. 60/061,279, Oct. 7, 1997.

[51] Int. Cl.[6] .............................. A61F 9/00; A45C 11/00
[52] U.S. Cl. ......................... 294/1.2; 294/64.1; 206/5.1
[58] Field of Search ................................... 294/1.2, 64.1; 206/5.1; 134/901; 606/107

[56] References Cited

U.S. PATENT DOCUMENTS

| | | | |
|---|---|---|---|
| 3,584,908 | 6/1971 | Ray | 294/1.2 |
| 3,645,576 | 2/1972 | Horres | 294/1.2 |
| 3,647,380 | 3/1972 | Middleton | 294/1.2 |
| 3,934,914 | 1/1976 | Carruthers | 294/1.2 |
| 4,079,976 | 3/1978 | Rainin | 294/1.2 |
| 4,123,098 | 10/1978 | Shoup | 294/1.2 |
| 4,126,345 | 11/1978 | List | 294/1.2 |
| 4,190,277 | 2/1980 | England | 294/1.2 |
| 4,223,782 | 9/1980 | Giambalvo | 206/5.1 |
| 4,520,923 | 6/1985 | Waldman | 206/5.1 |
| 4,753,470 | 6/1988 | Menard | 294/1.2 |
| 5,002,179 | 3/1991 | Dhalla | 206/5.1 |
| 5,069,494 | 12/1991 | Reinson et al. | 294/1.2 |
| 5,114,686 | 5/1992 | Gillespie | 422/300 |
| 5,236,236 | 8/1993 | Girimont | 294/1.2 |

FOREIGN PATENT DOCUMENTS

| | | | |
|---|---|---|---|
| 1431168 | 4/1976 | United Kingdom | 294/1.2 |

*Primary Examiner*—Dean J. Kramer
*Attorney, Agent, or Firm*—Eric Karich

[57] ABSTRACT

A contact lens insertion and manipulation assembly has a manipulation device, an insertion device, and an enclosure cap. The manipulation device includes a manipulator bulb made of a material to which the inside concave surface of the contact lens will lightly adhere. The manipulator device allows the user to remove the contact lens from the storage container without the user touching the contact lens. The manipulator bulb is shaped to support the contact lens in its proper shape, facilitating transfer of the lens to the insertion device. The insertion device includes a suction cup capable of removably engaging the outside convex surface of the contact lens and transferring the contact lens from the manipulator bulb to the user's eye. The insertion device and the manipulation device fit within the enclosure cap for compact and protected storage to prevent contamination. The assembly can then be used according to the described method of use to insert the contact lens into a user's eye without the user touching the contact lens with his fingers.

4 Claims, 4 Drawing Sheets

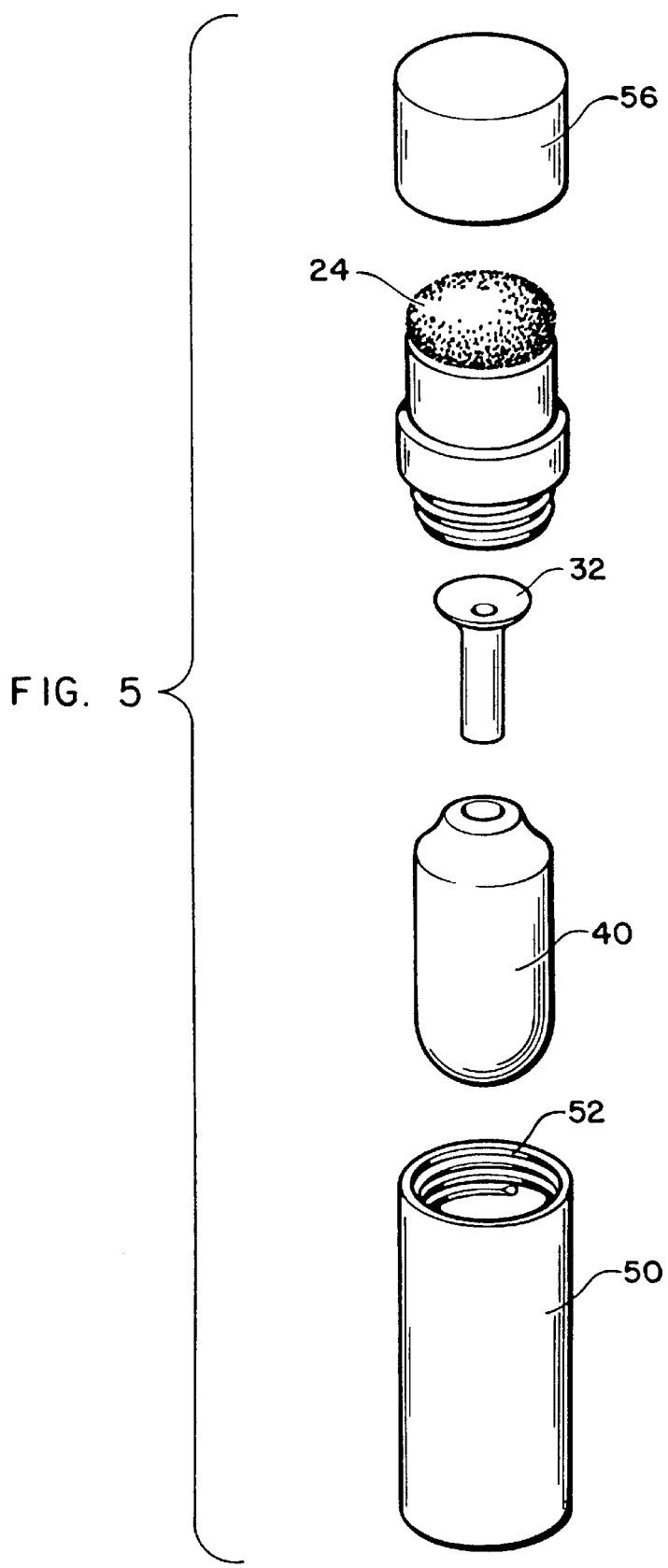

CONTACT LENS INSERTION AND MANIPULATION ASSEMBLY AND METHOD

This application for a utility patent follows a previously filed provisional patent having the Ser. No. 60/061,279 and a filing date of Oct. 7, 1997.

BACKGROUND OF THE INVENTION

1. Field of the Invention

This invention relates generally to tools for manipulating contact lenses, and more particularly to an assembly and method for manipulating a contact lens and inserting the contact lens into a user's eye without contaminating the contact lens.

2. Description of Related Art

Contact lenses have increased greatly in popularity in recent years. Unfortunately, as the number of users increases, the potential for harmful eye infections also increases. There is a recognized need for a tool to assist users in inserting their contact lenses into their eyes. It is especially important that the tool insert the contact lens into the user's eye in an uncontaminated condition to avoid eye infection. It is also important that the tool is safe and easy to use.

The traditional method of inserting contact lenses consists of placing the contact lens onto the user's fingertip and manually inserting the contact lens into the user's eye. There are several drawbacks to this method. First, the user's fingers often contaminate the contact lens. Second, the user's fingers may injure the user's eye if he pokes himself, especially if the user has long or jagged finger nails. Third, the contact lens will tend to fold, invert, and otherwise stick to the user's fingertip, making insertion impossible. If the contact lens does not adhere to the user's finger, it often simply falls off the user's finger and must be rinsed off so the user can try again. This handling and dropping on the ground further increases the risk of contamination and infection.

Many prior art devices have been devised to try to overcome these difficulties. Particularly relevant prior art patents include Schoup, U.S. Pat. No. 4,123,098, Rainin, U.S. Pat. No. 4,097,976, and Carruthers, U.S. Pat. No. 3,934,914, which disclose suction cup devices designed to removable hold the contact lens for insertion into the user's eye. Unfortunately, this still requires some handling of the contact lens by the user to mount the lens on the suction cup. Furthermore, these tools do not work with soft contact lenses and are generally restricted to use with hard contact lenses. This limitation is due to the flexible nature of soft contact lenses. It is nearly impossible to position a soft lens onto the suction cup of these prior art devices. The lens simply inverts, folds, and sticks to itself, failing to attain the correct shape necessary to conform to the suction cup. This limits the usefulness of these devices to hard contact lenses.

Other patents disclose devices that are claimed to be useful for soft contact lenses. Examples of these devices include England, U.S. Pat. No. 4,190,277, List, U.S. Pat. No. 4,126,345, and Horres, U.S. Pat. No. 3,645,576. These patents disclose various grasping and holding devices for soft contact lenses. These devices, however, are very difficult to use; they present a serious risk of poking the user's eyes and causing serious damage; and they still require the user to touch the contact lens with his or her fingers, seriously detracting from the benefit of the devices.

The prior art teaches various suction cups and other devices to hold a contact lens for insertion into the eye. However, the prior art does not teach a tool that allows the user to insert the contact without touching the lens. The prior art also does not teach a device that allows the user to insert a soft contact lens while minimizing the danger of the user damaging his eye with the insertion device. The present invention fulfills these needs and provides further related advantages as described in the following summary.

SUMMARY OF THE INVENTION

The present invention teaches certain benefits in construction and use which give rise to the objectives described below.

The present invention provides a contact lens insertion and manipulation assembly. The assembly includes an insertion device, a manipulation device, and preferably a means for enclosing the insertion and manipulation devices in a compact and protected assembly to prevent contamination. The manipulation device includes a manipulator bulb made of a material to which the inside concave surface of the contact lens will lightly adhere. The manipulator device allows the user to remove the contact lens from the storage container without the user touching the contact lens. The manipulator bulb is shaped to support the contact lens in its proper shape, facilitating transfer of the lens to the insertion device. The insertion device includes a suction cup capable of removably engaging the outside convex surface of the contact lens and transferring the contact lens from the manipulator bulb to the user's eye. The assembly can then be used to insert the contact lens into a user's eye without the user touching the contact lens with his fingers.

A primary objective of the present invention is to provide a contact lens insertion and manipulation assembly having advantages not taught by the prior art.

Another objective is to provide a manipulation device capable of removing the contact lens from the storage container and transferring the contact lens to an insertion device and then to the user's eye without the user touching the contact lens with his fingers.

A further objective is to promote the health and safety of the user by assisting him or her in avoiding contamination to his or her eyes through the use of contact lenses.

Other features and advantages of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention. In such drawings:

FIG. 5 shows an exploded perspective view of an alternative embodiment of the present invention.

DETAILED DESCRIPTION OF THE INVENTION

Figure 1:
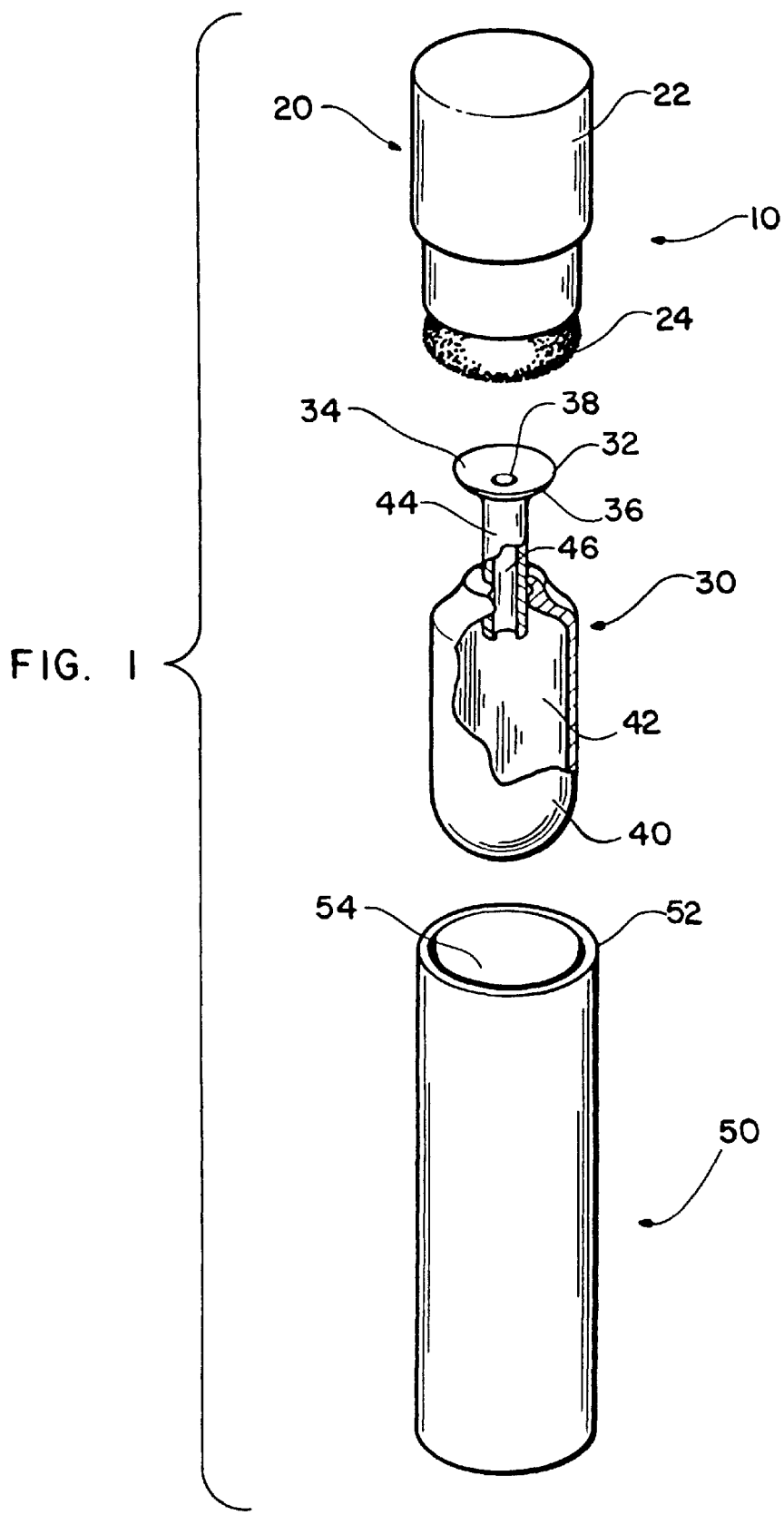
FIG. 1 is an exploded perspective partially cut-away view of the preferred embodiment of the present invention.

The above described drawing figures illustrate the invention, a contact lens insertion and manipulation assembly 10. The preferred embodiment of the assembly 10 is shown in FIG. 1. The assembly 10 includes a manipulation device 20, an insertion device 30, and a means for enclosing 50 the insertion device 30 and the manipulation device 20 to prevent contamination. The assembly 10 is useful for cleaning a contact lens 12 while it is still within a storage container 14. The assembly 10 can then be used to insert the contact lens 12 into a user's eye 16 without the user touching the contact lens 12 with his fingers. The method of using the assembly 10 is described more fully below and illustrated in FIGS. 2–4. An alternative embodiment of the assembly 10 is shown in FIG. 5.

The manipulation device 20, as shown in FIG. 1, includes a base portion 22 and a manipulator bulb 24. The base portion 22, preferably made of a rigid molded plastic, provides the user with a means for grasping the manipulator bulb 24; and the base portion 22 also interlocks with the means for enclosure as described below to store the manipulator bulb 24 in a protected enclosure shielded from contamination. The manipulator bulb 24 has a curved outer surface that matches the curve of the concave inner surface of the contact lens 12. When the contact lens 12 is adhering to the manipulator bulb 24, the manipulator bulb 24 supports the contact lens 12 in its correct shape, allowing the user to transfer the contact lens 12 to the insertion device 30 without the contact lens 12 folding, inverting, or otherwise losing its shape. The manipulator bulb 24 has an exterior surface to which the contact lens 12 will lightly adhere. After much experimentation, it has been found that the material best suited for this purpose is 100 PPI Premium Z natural reticulated polyurethane foam made of polyether and polyester cross-linked with polyurethane, although those skilled in the art can probably devise other suitable materials. The most preferred material is described in U.S. Pat. No. 5,460,665, herein incorporated by reference, and sold under the trademark CLEANWIPE WIPERS™, Model 4200, by Wilshire Technologies, Inc. in Carlsbad. This material is preferably pyrogen free and has a material density of 5.6±0.3 lbs. While a small ball of the material can be used, in its preferred embodiment only a layer of the material is used, the layer of the material covering a plastic base having the necessary curvature. It is preferred that only a layer of the material be used because this prevents the material from absorbing too much water from the lens storage container 14.

The insertion device 30, also shown in FIG. 1, includes a suction cup 32 shaped to receive the convex outer surface of the contact lens 12. The suction cup 32 is attached to a vacuum source 40 capable of producing a temporary and weak vacuum within the suction cup 32, causing the contact lens 12 to adhere to the suction cup 32. The vacuum source 40 is referred to as a resilient bulb 40 for the sake of clarity; however, it is understood that those skilled in the art could devise an alternative but equivalent structure. Similar structures are described in U.S. Pat. Nos. 4,123,098 and 4,079,976, herein incorporated by reference. The suction cup 32 preferably is attached to the resilient bulb 40 with a flexible tube 44. The suction cup 32 preferably has a concave surface 34, a back surface 36, and a vacuum hole 38 communicating therebetween. The concave surface 34 is shaped to receive the convex outer surface of the contact lens 12. The flexible tube 44 extends from the back surface 36 of the suction cup 32 to join the resilient bulb 40. The resilient bulb 40 has an internal vacuum cavity 42. The internal vacuum cavity 42 is in fluid communication with the vacuum hole 38 via a vacuum conduit 46 running through the flexible tube 44. The resilient bulb 40 is attached to the flexible tube 44 opposite the suction cup 32. The insertion device 30 is preferably made of molded plastic or rubber. The suction cup 32 is preferably made of a soft and flexible plastic that will not scratch the user's eye 16. The flexible tube 44 is preferably made of a soft and flexible plastic to prevent an accidental poking injury to the user's eye 16. In its most preferred embodiment, the flexible tube 44 is made of a Styrene Bloc Copolymer (S-EB-S), sold under the trademark KRATON DYNOFLEX™ polymer by GLS Corporation, of Cary, Ill. This material is soft enough so it will not damage the user's eye upon a poking accident. The resilient bulb 40 is preferably made of a resilient plastic or rubber that is easily grasped and manipulated by the user. This structure allows the user to squeeze the resilient bulb 40 and, upon releasing the resilient bulb 40, create a weak vacuum at the concave surface of the suction cup 32. This allows the user to hold a soft contact lens 12 without using his or her fingers. Once the contact lens 12 is so held, the user can easily insert the contact into his or her eye 16 without contamination.

The invention further includes a means for enclosing 50 the insertion device 30 and the manipulation device 20 to prevent contamination. Those skilled in the art can easily devise many different configurations for accomplishing this goal without deviating from the scope of this invention. In the preferred embodiment, as shown in FIG. 1, the means for enclosing 50 includes an enclosure cap 50 having an aperture 52 communicating with an internal chamber 54. The insertion device 30 preferably fits within the internal chamber 54 of the enclosure cap 50; and the base portion 22 of the manipulation device 20 removably engages the aperture 52 to seal the manipulator bulb 24 and the insertion device 30 within the internal chamber 54 of the enclosure cap 50. The base portion 22 preferably engages the aperture 52 with a frictional fit, although alternative methods such as a threaded engagement are acceptable. The entire means for enclosing 50 is preferably made of molded plastic. In an alternative embodiment, as shown in FIG. 5, the manipulator bulb 24 does not fit within the internal chamber 54 of the enclosure cap 50. Instead, the manipulator bulb 24 is covered by a separate top cap 56.

Figure 2:
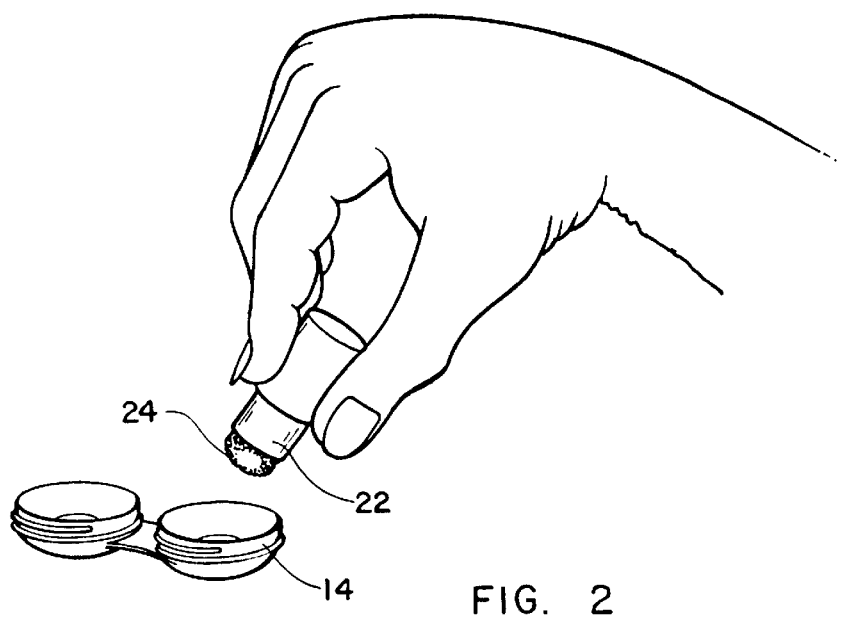
FIG. 2 is a perspective view of a manipulation device being used to remove a contact lens from a contact lens storage container.

This invention also includes a method for manipulating and inserting a contact lens 12 with the above-described manipulation and insertion assembly 10. The method first requires the user to provide the above-described manipulation and insertion assembly 10, along with a contact lens 12 in a storage container 14. After removing the manipulation device 20 and the insertion device 30 from the means for enclosing 50, the user is ready to use the manipulation device 20 to remove the contact lens 12 from the storage container 14 and transfer the contact lens 12 to the insertion device 30. As shown in FIG. 2, the user inserts the manipulator bulb 24 into the storage container 14, thereby causing the contact lens 12 to removably adhere to the manipulator bulb 24. Since the shape of the manipulator bulb 24 is similar to the shape of the contact lens 12, the manipulator bulb 24 supports the contact lens 12 in its proper shape, thereby preventing the contact lens 12 from folding or inverting. At this point, the user preferably swirls the manipulator bulb 24 around the storage container 14 to wash the contact lens 12 and remove particles from the inside of the contact lens 12. By lifting the manipulation device 20, the user removes the contact lens 12 from the storage container 14 in anticipation of inserting the contact lens 12 into his or her eye 16.

Figure 3:
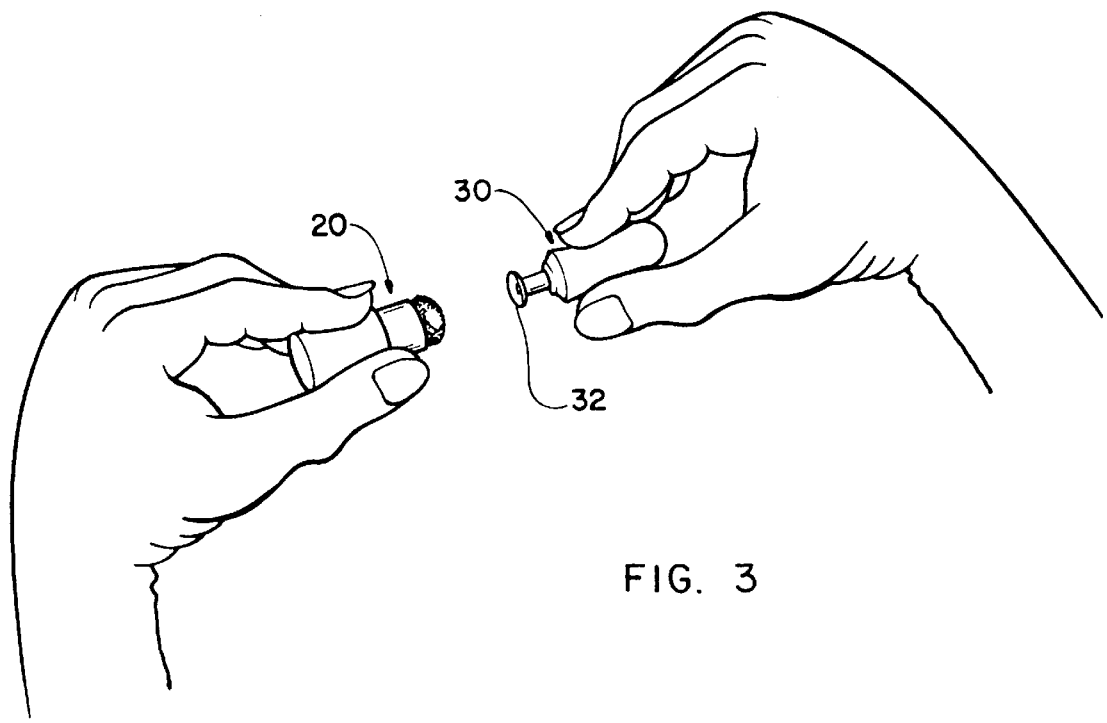
FIG. 3 is a perspective view of an insertion device being used to remove the contact lens from the manipulation device.
Figure 4:
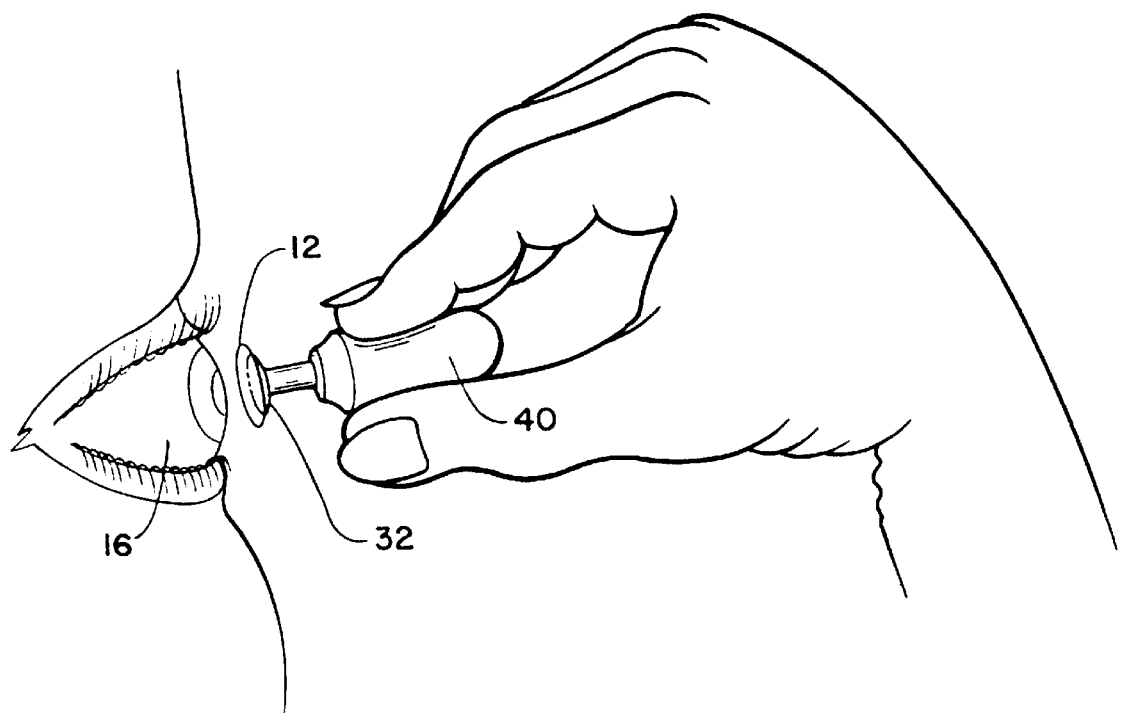
FIG. 4 is a side elevational view of the insertion device being used to insert the contact into the user's eye.

As shown in FIG. 3, the user then uses the insertion device 30 to insert the contact lens 12 into his or her eye 16. To accomplish this, the user squeezes the resilient bulb 40, touches the concave surface 34 of the suction cup 32 to the contact lens 12, and releases the resilient bulb 40, thereby creating a vacuum in the suction cup 32 and causing the contact lens 12 to adhere to the suction cup 32. Since the manipulator bulb 24 supports the contact lens 12 in its proper shape, it is easy to transfer the contact lens 12 to the insertion device 30 without the contact lens 12 folding or inverting. Once the contact lens 12 is adhering to the suction cup 32, the user removes the contact lens 12 from the manipulator bulb 24 with the insertion device 30. As shown in FIG. 4, the user then touches the contact lens 12 to his eye 16, causing the contact lens 12 to adhere thereto. By squeezing the resilient bulb 40, the user is able to thereby release the contact lens 12 from the insertion device 30. The contact lens 12 then remains adhered to the user's eye 16. By following this method, the user is able to remove the contact lens 12 from the storage container 14 and insert the contact lens 12 into his or her eye 16 without touching the lens with his or her fingers.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A contact lens insertion and manipulation assembly comprising:
   (a) a manipulation device having
      a base portion; and
      a manipulator bulb shaped to conform to the interior surface of the contact lens, the manipulator bulb being made of a material to which the contact lens will lightly adhere; and
   (b) an insertion device having
      a suction cup shaped to receive the exterior surface of the contact lens;
      a resilient bulb having an internal vacuum cavity that is in fluid communication with the suction cup, thereby being capable of producing a vacuum between the suction cup and the contact lens; and
   (c) an enclosure cap having an internal chamber with an aperture, the insertion device fitting within the internal chamber of the enclosure cap, the base portion of the manipulation device removably engaging the aperture to seal the manipulator bulb and the insertion device within the internal chamber of the enclosure cap.

2. A method for manipulating and inserting a contact lens, the method comprising the steps of:
   (a) providing a manipulation and insertion assembly having
      a manipulation device having a base portion; and a manipulator bulb shaped to conform to the interior surface of the contact lens, the manipulator bulb being made of a material to which the contact lens will lightly adhere; and
      an insertion device having a suction cup shaped to receive the exterior surface of the contact lens; and a resilient bulb having an internal vacuum cavity that is in fluid communication with the suction cup, thereby being capable of producing a vacuum between the suction cup and the contact lens;
   (b) providing a contact lens in a storage container;
   (c) inserting the manipulator bulb into the storage container, thereby causing the interior surface of the contact lens to removably adhere to the manipulator bulb;
   (d) squeezing the resilient bulb;
   (e) touching the suction cup to the exterior surface of the contact lens;
   (f) releasing the resilient bulb, thereby creating a vacuum in the suction cup and causing the contact lens to adhere to the suction cup;
   (g) removing the contact lens from the manipulator bulb with the insertion device;
   (h) touching the contact lens to a user's eye; and
   (i) squeezing the resilient bulb, thereby releasing the contact lens from the insertion device and releasing the contact lens into the user's eye.

3. The method of claim 2 further comprising the step of:
   (c') swirling the manipulator bulb around the storage container thereby washing the contact lens.

4. The method of claim 2 further comprising the step of:
   (a') providing a means for enclosing the insertion device and the manipulation device to prevent contamination; and
   (b') removing the manipulation device and the insertion device from the means for enclosing.

* * * * *